(12) United States Patent
Varela et al.

(10) Patent No.: US 9,421,054 B2
(45) Date of Patent: *Aug. 23, 2016

(54) INTERLOCKING BIOMEDICAL IMPLANT FASTENER AND WASHER CONCEPTS

(71) Applicant: US Spine, Inc., Salt Lake City, UT (US)

(72) Inventors: Armando Varela, Boca Raton, FL (US); Doris Blake, Delray Beach, FL (US); Trace R. Cawley, Austin, TX (US); Peter Harris, Boca Raton, FL (US)

(73) Assignee: US SPINE, INC., Salt Lake City, UT (US)

( * ) Notice: Subject to any disclaimer, the term of this patent is extended or adjusted under 35 U.S.C. 154(b) by 46 days.

This patent is subject to a terminal disclaimer.

(21) Appl. No.: 14/462,342

(22) Filed: Aug. 18, 2014

(65) Prior Publication Data

US 2014/0358184 A1 Dec. 4, 2014

Related U.S. Application Data

(63) Continuation of application No. 12/579,667, filed on Oct. 15, 2009, now Pat. No. 8,808,339.

(60) Provisional application No. 61/105,545, filed on Oct. 15, 2008.

(51) Int. Cl.
| | | |
|---|---|---|
| *A61B 17/04* | (2006.01) | |
| *A61B 17/86* | (2006.01) | |
| *A61F 2/08* | (2006.01) | |
| *A61B 17/88* | (2006.01) | |

(52) U.S. Cl.
CPC ............ *A61B 17/8695* (2013.01); *A61B 17/862* (2013.01); *A61B 17/864* (2013.01); *A61B 17/8605* (2013.01); *A61B 17/8872* (2013.01); *A61B 17/8891* (2013.01); *A61B 2017/8655* (2013.01)

(58) Field of Classification Search
CPC ........... A61B 17/8695; A61B 17/8605; A61B 17/864; A61B 17/862; A61B 17/8891; A61B 17/8872; A61B 2017/8655
USPC ......... 606/247, 264–275, 288–290, 300–321; 411/114, 138, 149, 327, 332
See application file for complete search history.

(56) References Cited

U.S. PATENT DOCUMENTS

| | | | | |
|---|---|---|---|---|
| 2003/0105465 A1* | 6/2003 | Schmieding | ....... | A61B 17/0401 606/916 |
| 2003/0216735 A1* | 11/2003 | Altarac | ............. | A61B 17/7037 606/266 |
| 2006/0266168 A1* | 11/2006 | Pacheco | ................ | B25B 13/065 81/460 |

* cited by examiner

*Primary Examiner* — Christopher Beccia
*Assistant Examiner* — Diana S Jones
(74) *Attorney, Agent, or Firm* — Phillips Ryther & Winchester; Matthew D. Thayne

(57) ABSTRACT

Biomedical implant fastener systems, such as bone screw systems and the like. In some embodiments, a fastener may comprise a first plurality of teeth, and a washer configured to be received on the fastener may comprise a second plurality of teeth configured to be engaged with the first plurality of teeth. The first plurality of teeth may be configured to engage with the second plurality of teeth such that so as to allow for selective rotation between the washer and the fastener in a first rotational direction and so as to prevent rotation between the washer and the fastener in a second rotational direction opposite from the first rotational direction when the fastener is engaged with the washer such that second plurality of teeth is engaged with the first plurality of teeth so as to prevent the fastener from backing out of the washer after engagement.

22 Claims, 15 Drawing Sheets

INTERLOCKING BIOMEDICAL IMPLANT FASTENER AND WASHER CONCEPTS

RELATED APPLICATIONS

This application is a continuation of U.S. patent application Ser. No. 12/579,667, filed on Oct. 15, 2009 and titled "INTERLOCKING BONE SCREW AND WASHER CONCEPTS," which claims the benefit of priority of U.S. Provisional Patent Application No. 61/105,545, filed on Oct. 15, 2008 and titled "INTERLOCKING BONE SCREW AND WASHER CONCEPTS," the entire contents both of which are hereby incorporated by reference herein.

FIELD OF THE INVENTION

The present invention relates generally to a surgically-implantable spinal or other anatomical assembly. More specifically, in some embodiments, the present invention relates to a biomedical implant fastener system, such as a cannulated bone screw system.

BACKGROUND OF THE INVENTION

In various cases, it is desirable to immobilize a facet joint of the spine (e.g. in support of a spinal fusion, etc.) by means other than conventional pedicle screw systems. A variety of surgically-implantable devices and assemblies have been developed in order to address such cases. Typically, these devices and assemblies utilize a single transfacet bolt or the like that is disposed through a bore drilled through the superior and inferior facets of the facet joint. However, not all spinal morphologies support the utilization of such a transfacet bolt, and the utilization of such a transfacet bolt can be clumsy depending upon the application. In such cases, the use of an alternative device or assembly is desirable. However, no such alternative devices or assemblies are currently available or in existence.

BRIEF SUMMARY OF THE INVENTION

In an exemplary embodiment of the present invention, a cannulated bone screw system includes a screw with a threaded portion, a non-threaded portion, and a first plurality of teeth spaced apart from a screw head; and a washer with an interior portion with a second plurality of teeth and an opening and an outer portion with a plurality of spikes. The first plurality of teeth are on an inferior convex surface; wherein the second plurality of teeth are on a superior concave surface; and wherein the first plurality of teeth and the second plurality of teeth are operable to mate to prevent the screw from backing out of the washer while allowing the cannulated bone screw system to conform/pivot in order to accommodate different bone morphologies. The screw head can include keyed flanged heads. The cannulated bone screw system can further include a screw holder operable to engage the keyed flanged heads. Optionally, the cannulated bone screw system further includes a screw holder assembly disposed to the screw holder. Alternatively, the cannulated bone screw system further includes a rescue screw assembly disposed to the screw holder. The plurality of spikes are operable to engage a bone. The screw can be driven into the washer positioned at a pilot hole in a bone at an angle. Optionally, the bone includes a first facet joint and a second facet joint; wherein the pilot hole is located on the first facet joint; wherein the plurality of spikes are engaged to the first facet joint; and wherein the threaded portion is positioned within the second facet joint. The cannulated bone screw system can further include a drill guide and washer holder comprising an end clasping mechanism. Optionally, the end clasping mechanism includes an inserter tube that contains the washer.

In another exemplary embodiment of the present invention, a cannulated bone screw system includes a screw with a threaded portion, a non-threaded portion, and a first plurality of teeth spaced apart from a screw head; and a washer with an interior portion with a second plurality of teeth and an opening and an outer portion with a plurality of spikes; wherein the second plurality of teeth are on a superior concave surface; and wherein the first plurality of teeth and the second plurality of teeth are operable to mate to prevent the screw from backing out of the washer while allowing the cannulated bone screw system to conform/pivot in order to accommodate different bone morphologies. The cannulated bone screw system can further include means for holding the screw, means for positioning the washer, means for drilling a pilot hole, and means for inserting the screw into the pilot hole.

In yet another exemplary embodiment of the present invention, a method of screwing a cannulated bone screw into a bone includes positioning a washer on the bone; drilling a pilot hole; engaging a cannulated bone screw; positioning the cannulated bone screw at the pilot hole; screwing the cannulated bone screw into the pilot hole; engaging the cannulated bone screw to the washer; and applying rotational force to drive a plurality of spikes on the washer into the bone. The cannulated bone screw can include a first plurality of teeth spaced apart from a screw head; and the washer can include an interior portion with a second plurality of teeth and an opening and an outer portion with the plurality of spikes. The first plurality of teeth are on an inferior convex surface; wherein the second plurality of teeth are on a superior concave surface; and wherein the first plurality of teeth and the second plurality of teeth are operable to mate to prevent the screw from backing out of the washer while allowing the cannulated bone screw system to conform/pivot in order to accommodate different bone morphologies.

BRIEF DESCRIPTION OF THE DRAWINGS

The present invention is illustrated and described herein with reference to the various drawings, m which like reference numbers denote like system components/method steps, as appropriate, and in which.

DETAILED DESCRIPTION OF THE INVENTION

Figure 1:
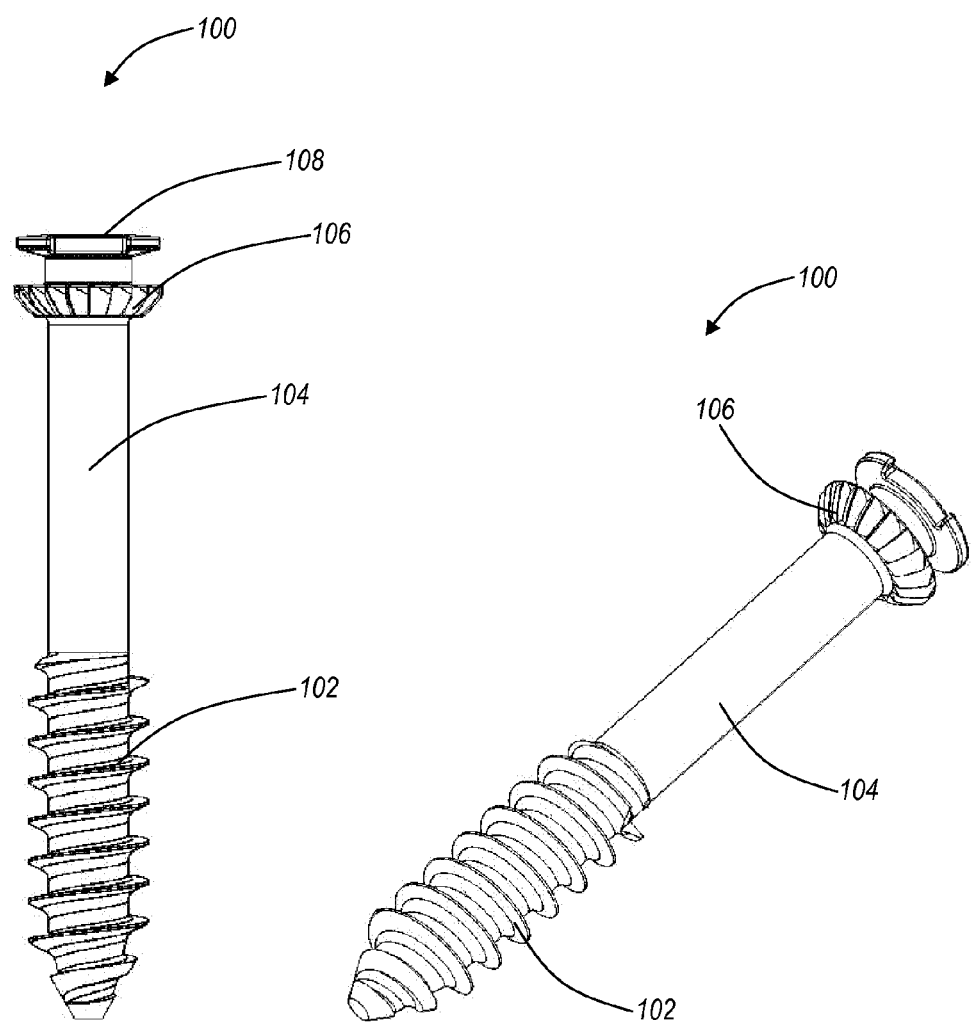
FIG. 1 illustrates different views of a cannulated bone screw according to an exemplary embodiment of the present invention.

Referring to FIG. 1, different views are illustrated of a cannulated bone screw 100 according to an exemplary embodiment of the present invention. The cannulated bone screw 100 includes a threaded end portion 102, a non-threaded portion 104, and a radial interlocking convex toothed surface 106 disposed near a screw head 108. The threaded end portion 102 is operable to screw into a bone, such as a facet joint or the like. The cannulated bone screw 100 can be utilized to stabilize facet joints through an angular insertion of the cannulated bone screw 100 into a first facet and screwing the cannulated bone screw 100 into a second facet, the associated pedicle, or any other bony structure. Once fully engaged between the facets, the associated pedicle, or any other bony structure, the threaded portion 102 is embedded in the second facet, the associated pedicle, or any other bony structure, and the non-threaded portion 104 is in the first facet. Additionally, a washer (FIG. 3) is operable to engage the screw head 108 and an outer surface of the first facet. It should be noted that any suitable guide holes or bores can be utilized in achieving the placement/securement of the cannulated bone screw 100.

Figure 2:
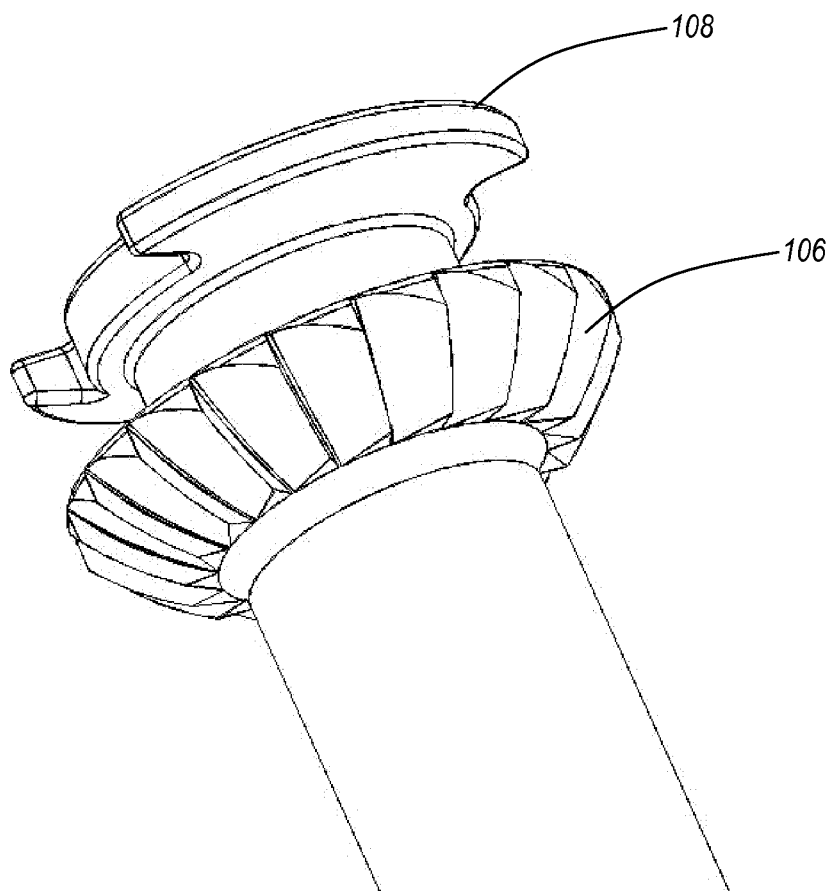
FIG. 2 illustrates a close up view of the radial interlocking convex toothed surface and the screw head of the cannulated bone screw of FIG. 1 according to an exemplary embodiment of the present invention.
Figure 3:
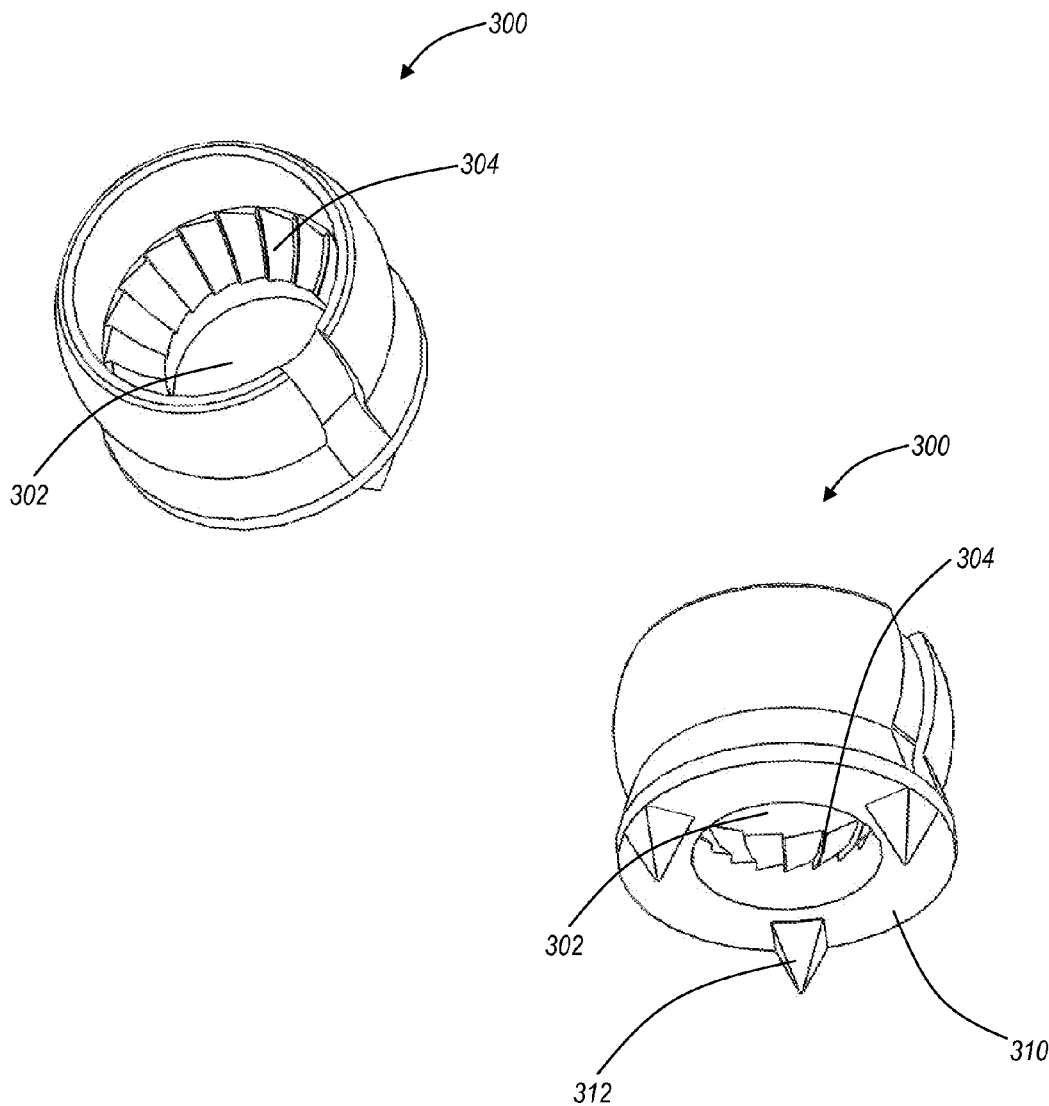
FIG. 3 illustrates different views of a washer for mating with the cannulated bone screw of FIG. 1 according to an exemplary embodiment of the present invention.

Referring to FIG. 2, a close up view illustrates the radial interlocking convex toothed surface 106 and the screw head 108 of the cannulated bone screw 100 according to an exemplary embodiment of the present invention. The screw head 108 includes a unique slotted head flange that holds and drives the cannulated bone screw 100 into a facet joint or the like. The unique head flange design holds bone screw 100 securely as well as permitting initial thread engagement into a pilot hole. The radial interlocking convex toothed surface 106 includes a radial toothed pattern on an inferior convex surface that is configured to mate with a superior concave surface of a washer, as depicted in FIG. 3. Any suitable radial toothed pattern and mating superior concave surface can be utilized, as long as relative rotational between the two structures is selectively prevented upon engagement.

Referring to FIG. 3, different views are illustrated of a washer 300 for mating with the cannulated bone screw 100 according to an exemplary embodiment of the present invention. The washer 300 includes a concentric shape dimensioned responsive to the cannulated bone screw 100. The washer 300 includes an opening 302 for receiving the threaded end portion 102 and the non-threaded portion 104 of the cannulated bone screw 100. An interior of the washer 300 includes an interlocking radial toothed pattern on a superior concave surface 304. The superior concave surface 304 is configured to mate with the inferior convex surface on the radial interlocking convex toothed surface 106. The interlocking teeth between the washer 300 and the screw head 108 advantageously prevent rotational loosening of the cannulated bone screw 100. A bottom portion 310 of the washer 300 includes a plurality of spikes 312. The plurality of spikes 312 are configured to engage a bone when the cannulated bone screw 100 and the washer 300 are screwed into the bone. It should be noted that, throughout, spikes can be replaced with any suitable frictional surface for preventing movement and/or rotation.

Figure 4:
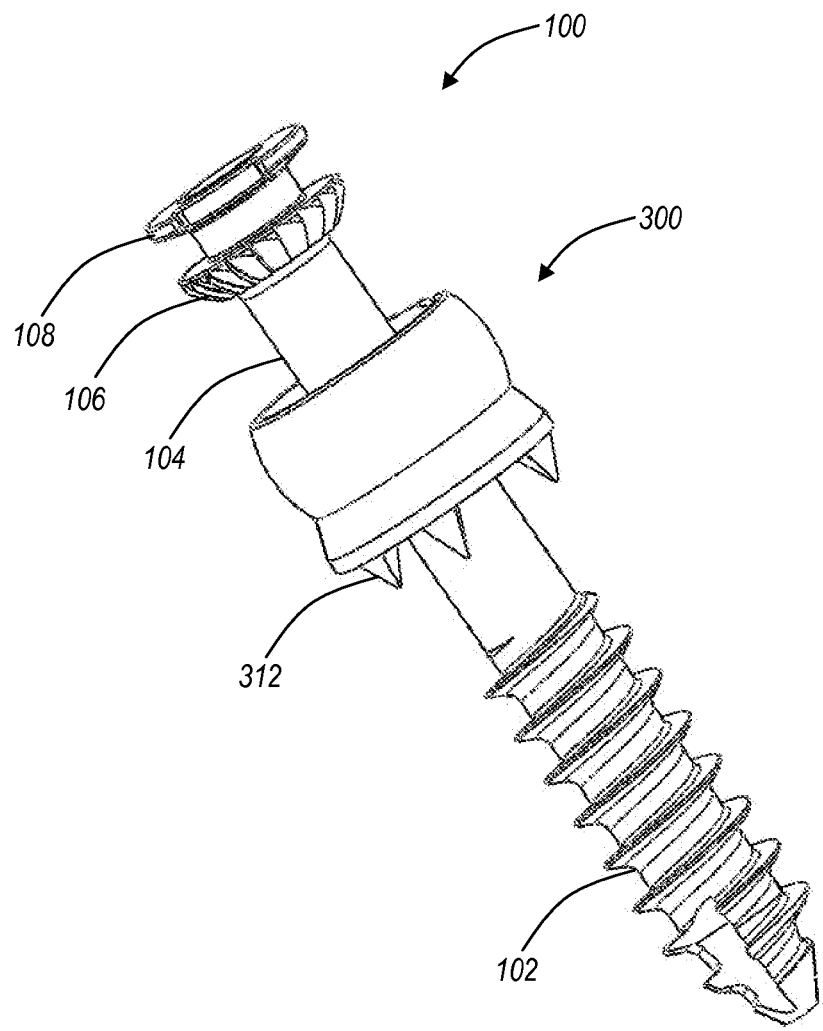
FIG. 4 illustrates the cannulated bone screw of FIG. 1 engaged with the washer of FIG. 3 according to an exemplary embodiment of the present invention.

Referring to FIG. 4, the cannulated bone screw 100 is illustrated engaged with the washer 300 according to an exemplary embodiment of the present invention. The opening 302 of the washer 300 is slid over the threaded portion 102 to the non-threaded portion 104. As the threaded portion 102 is screwed into a bone, the spikes 312 on the washer 300 engage the bone, and the washer 300 engages the radial interlocking convex toothed surface 106 on the cannulated bone screw 100. In the locked position, the interlocking concave/convex surfaces on the toothed surface 106 and the washer 300 prevent the screw from backing out while allowing the cannulated bone screw 100 to conform/pivot in order to accommodate different bone morphologies.

Figure 5:
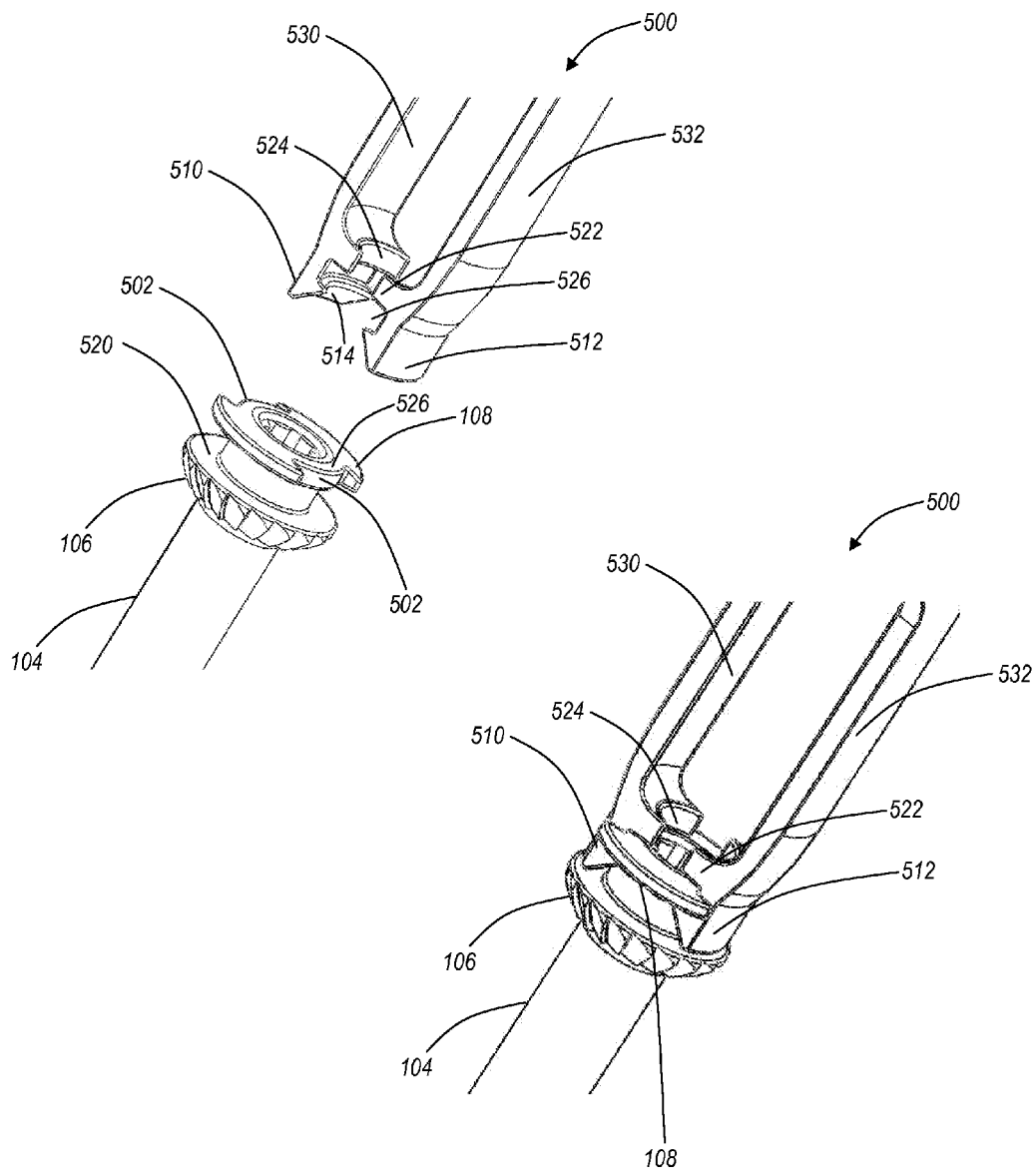
FIG. 5 illustrates a screw holder for engaging the screw head of the cannulated bone screw of FIG. 1 according to an exemplary embodiment of the present invention.

Referring to FIG. 5, a screw holder 500 is illustrated for engaging the screw head 108 according to an exemplary embodiment of the present invention. FIG. 5 illustrates the screw holder 500 disengaged from and engaged to the screw head 108. The screw holder 500 is configured to snap over keyed head flanges 502 in the screw head 108. The screw holder 500 includes a first arc member 510 and a second arc member 512, each configured to engage one of the keyed head flanges 502 in the screw head 108. The arc members 510, 512 each include a notch 514 which snaps on the keyed head flanges 502, and a top of the arc members 510, 512 substantially mates with a top side 520 of the toothed surface 106. The screw holder 500 further includes a first arc portion 522 and a second arc portion 524 offset from the arc members 510, 512. The arc portions 522, 524 are operable to engage a top 526 of the screw head 108 when the arc members 510, 512 are engaged to the keyed head flanges 502. Collectively, the arc members 510, 512 and the arc portions 522, 524 define notches 526 which are operable to engage the keyed head flanges 502. In the engaged position, the screw holder 500 is operable to translate a rotational force to the cannulated bone screw 100 to enable engagement of the washer 300 and a bone. The screw holder 500 also further includes a first support member 530 and a second support member 532. Each of the support members 530, 532 are disposed to the arc members 510, 512, and the arc portions 522, 524 extend from the support members 530, 532.

Figure 6:
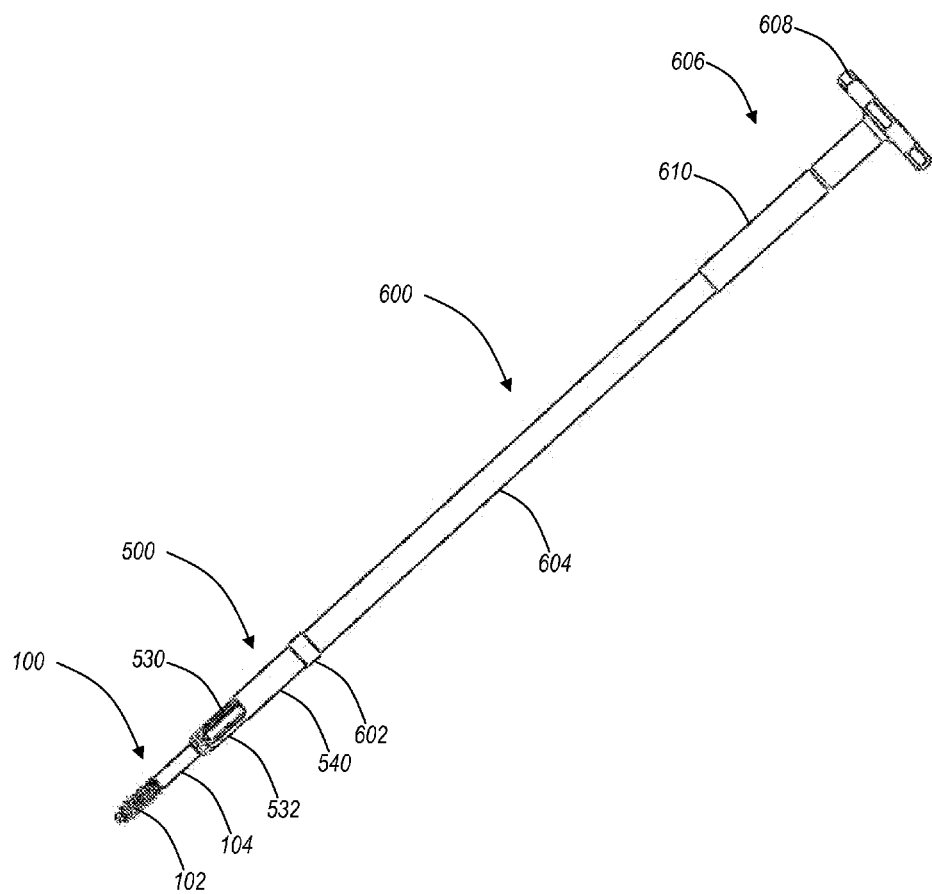
FIG. 6 illustrates a bone screw and screw holder assembly according to an exemplary embodiment of the present invention.

Referring to FIG. 6, a bone screw and screw holder assembly 600 is illustrated according to an exemplary embodiment of the present invention. The bone screw and screw holder assembly 600 is operable to engage the screw holder 500 and the cannulated bone screw 100 for insertion into a bone. The support members 530, 532 of the screw holder 500 are each disposed to a cylinder section 540. The cylinder section 540 engages a coupling mechanism 602 which enables the bone screw and screw holder assembly 600 to engage the screw holder 500. Note, the coupling mechanism 602 can be disposed on the screw holder 500, on the bone screw and screw holder assembly 600, or separate from both. The coupling mechanism 602 is configured to provide engagement between the screw holder 500 and the bone screw and screw holder assembly 600. A cylinder portion 604 of the bone screw and screw holder assembly 600 extends from the coupling mechanism 602 to a handle portion 606. The handle portion 606 can include a T-shaped handle 608 and a grip portion 610. In operation, a surgeon utilizes the bone screw and screw holder assembly 600 to engage the screw holder 500 and the cannulated bone screw 100. The handle portion 606 enables the surgeon to insert the threaded portion 102 and the non-threaded portion 104 into a bone.

Figure 7:
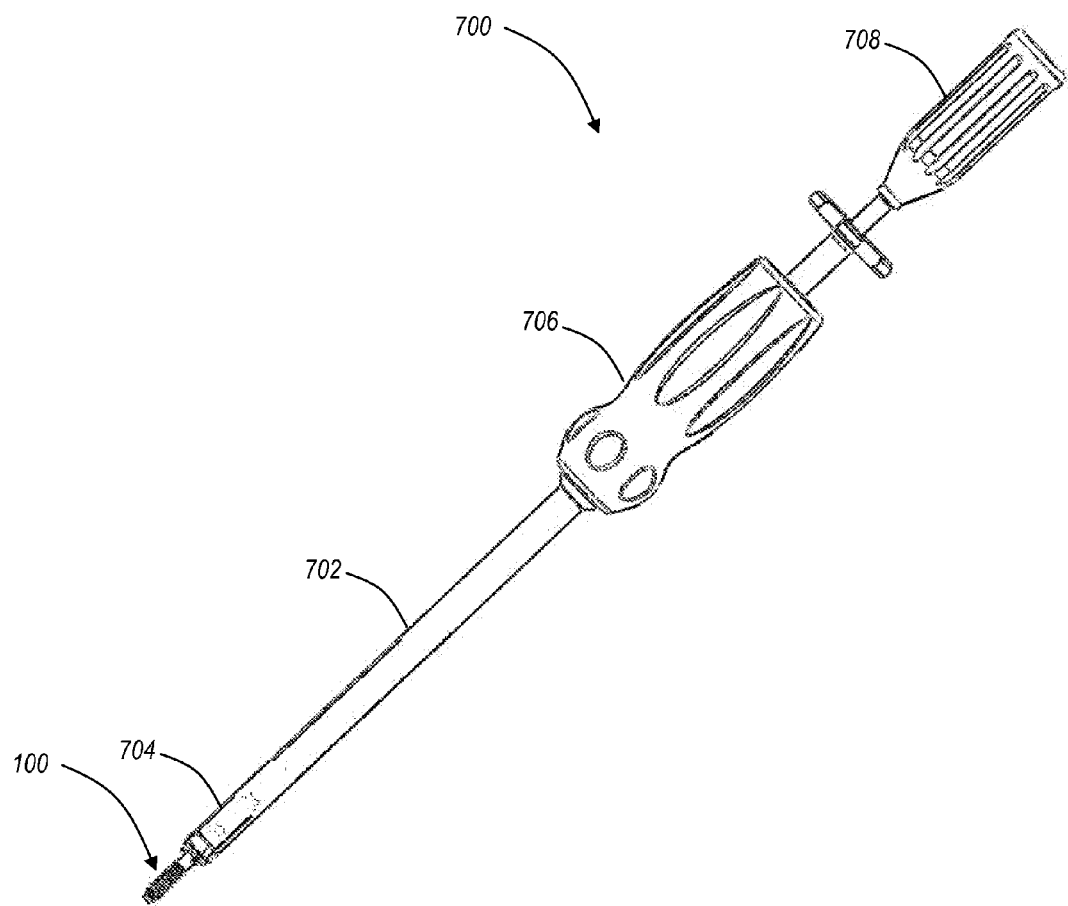
FIG. 7 illustrates a rescue screw system assembly for removing the cannulated bone screw of FIG. 1 according to an exemplary embodiment of the present invention.

Referring to FIG. 7, a rescue screw system assembly 700 is illustrated for removing the cannulated bone screw 100 according to an exemplary embodiment of the present invention. The rescue screw system assembly 700 engages the cannulated bone screw 100 in a similar fashion as the screw holder 500 as described in FIG. 5. The rescue screw system assembly 700 includes a cylinder member 702 disposed to an engagement mechanism 704 at one end. The engagement mechanism 704 is configured to engage the cannulated bone screw 100. A grip portion 706 is disposed at another end of the cylinder member 702. A handle portion 708 is disposed to the grip portion 706. Collectively, a surgeon can utilize the grip portion 706 and the handle portion 708 to maneuver the rescue screw system assembly 700 to engage the cannulated bone screw 100, and to subsequently remove the cannulated bone screw 100 through rotational force imposed through the grip portion 706 and the handle portion 708.

Figure 8:
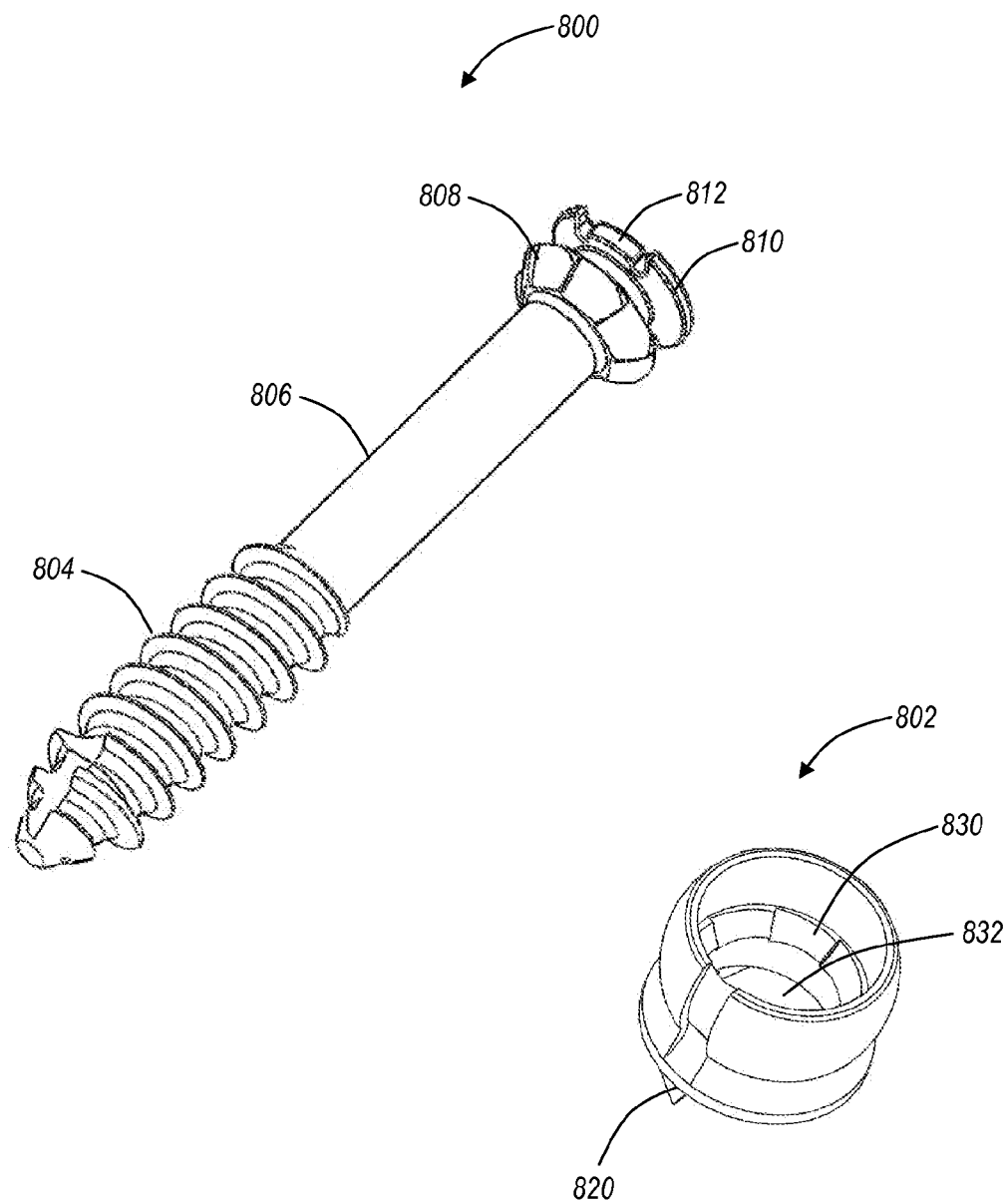
FIG. 8 illustrates a cannulated bone screw and a washer according to another exemplary embodiment of the present invention.

Referring to FIG. 8, a cannulated bone screw 800 and a washer 802 are illustrated according to an exemplary embodiment of the present invention. The cannulated bone screw 100 includes a threaded end portion 804, a non-threaded portion 806, and a radial interlocking convex toothed surface 808 disposed near a screw head 810. The screw head 810 includes keyed head flanges 812 for engaging a screw holder, drill, or the like. The threaded end portion 804 is operable to screw into a bone, such as a facet joint or the like. The cannulated bone screw 800 can be utilized to stabilize facet joints through an angular insertion of the cannulated bone screw 800 into a first facet and screwing the cannulated bone screw 800 into a second facet, the associated pedicle, or any other bony structure. Once fully engaged between the facets, pedicle, or other bony structure, the threaded portion 804 is embedded in the second facet, the associated pedicle, or any other bony structure, and the non-threaded portion 806 is in the first facet. Additionally, the washer 802 is operable to engage the screw head 108 and an outer surface of the first facet through a plurality of spikes 820 located on a bottom side of the washer 802. An interior of the washer 802 includes an interlocking radial toothed pattern 830 on a superior concave surface. The washer 802 further includes an opening 832 dimensioned to receive the cannulated bone screw 800. The interlocking radial toothed pattern 830 is operable to engage the radial interlocking convex toothed surface 808 to prevent rotational loosening of the cannulated bone screw 800.

Figure 9:
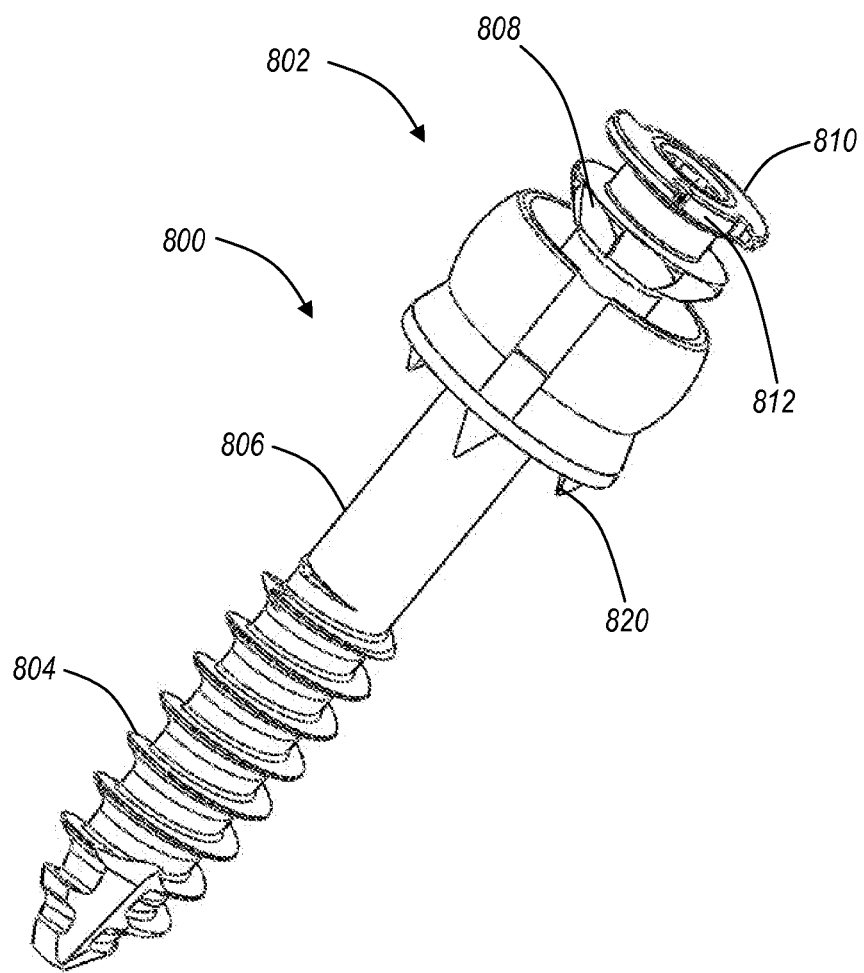
FIG. 9 illustrates the cannulated bone screw engaged with the washer according to an exemplary embodiment of the present invention.

Referring to FIG. 9, the cannulated bone screw 800 is illustrated engaged with the washer 802 according to an exemplary embodiment of the present invention. The opening 832 of the washer 800 is slid over the threaded portion 804 to the non-threaded portion 806. As the threaded portion 804 is screwed into a bone, the spikes 820 on the washer 802 engage the bone, and the washer 802 engages the radial interlocking convex toothed surface 808 on the cannulated bone screw 800. In the locked position, the interlocking concave/convex surfaces on the toothed surface 808 and the washer 802 prevent the screw from backing out while allowing the cannulated bone screw 800 to conform/pivot in order to accommodate different bone morphologies.

Figure 10:
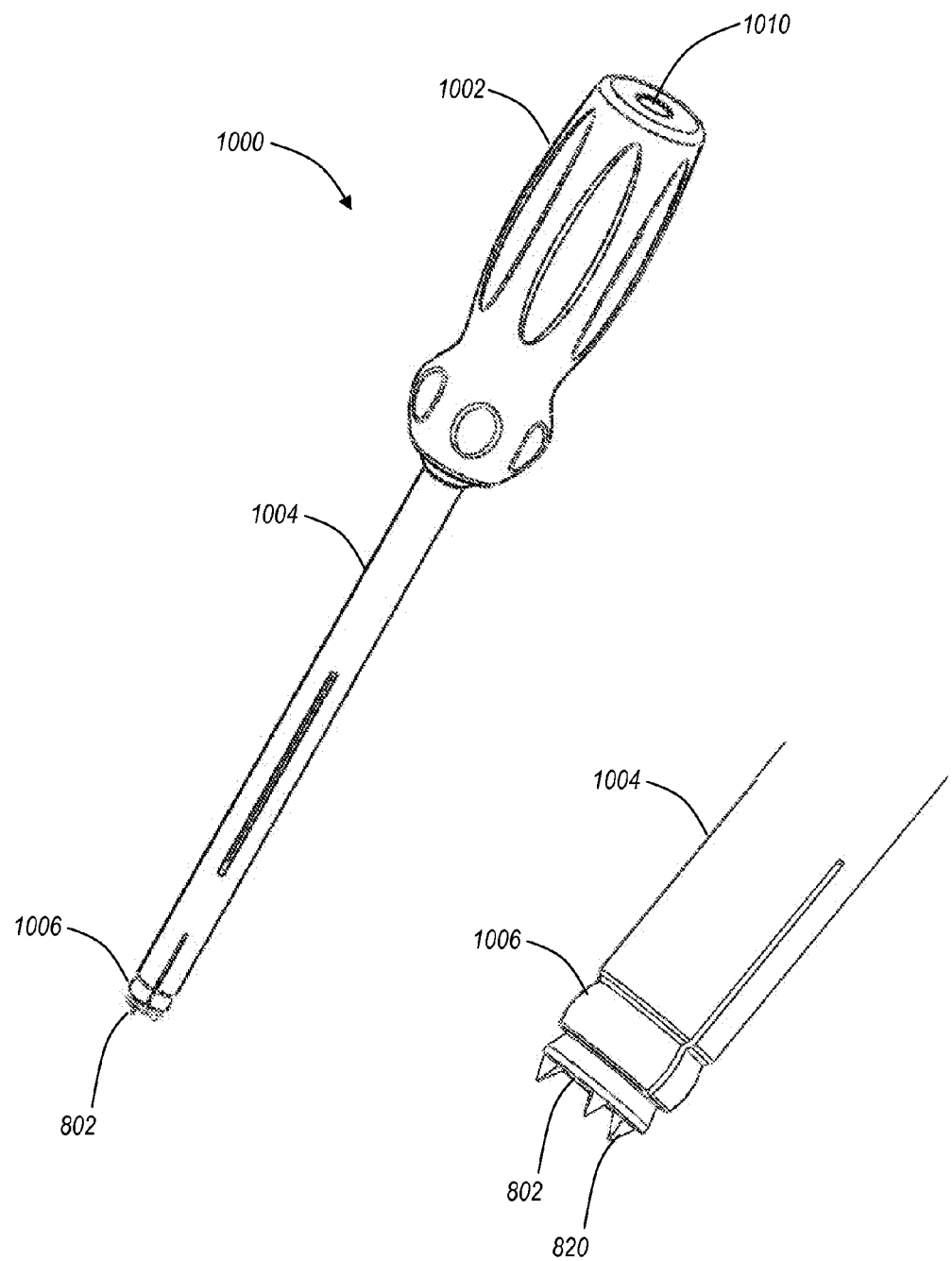
FIG. 10 illustrates a drill guide and washer holder according to an exemplary embodiment of the present invention.

Referring to FIG. 10, a drill guide and washer holder 1000 is illustrated according to an exemplary embodiment of the present invention. The drill guide and washer holder 1000 is operable to place the washer 802 on a surface, i.e. bone, and to guide a drill with the cannulated bone screw 800 through the washer 802 and the bone. The drill guide and washer holder 1000 includes a handle portion 1002, a cylinder member 1004 disposed to the handle portion 1002, and an end clasping mechanism 1006 disposed to an end of the cylinder member 1004. The end clasping mechanism 1006 is configured to grasp and place the washer 802. For example, the end clasping mechanism 1006 can include an inserter tube that contains the washer 802. The handle portion 1002 includes a drill opening 1010 operable to receive a drill. The opening 1010 extends through the handle portion 1002, the cylinder member 1004, and the end clasping mechanism 1006 to enable the drill to engage the washer 802 and extend out of the end clasping mechanism 1006 to a bony structure or the like.

Figure 11:
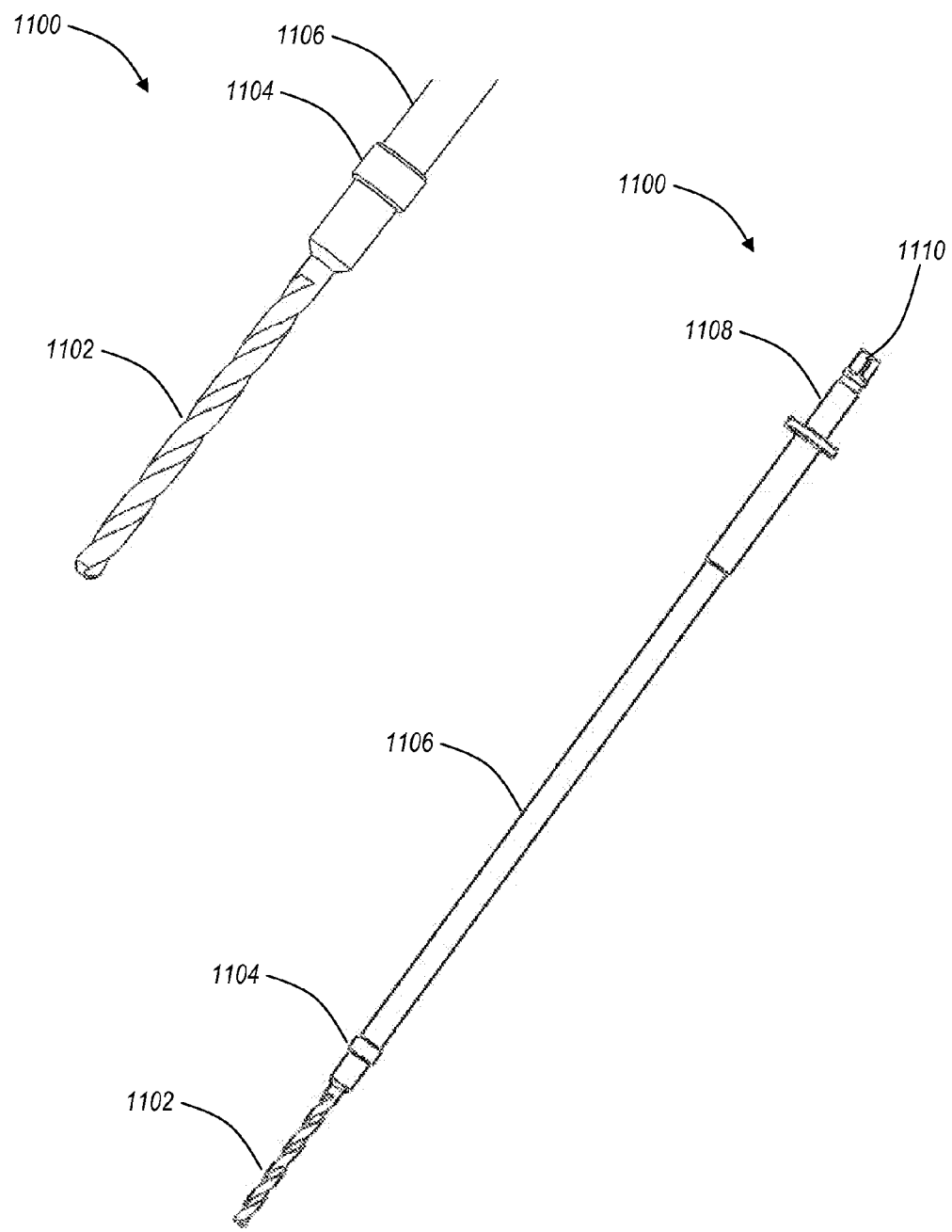
FIG. 11 illustrates different views of a cannulated drill according to an exemplary embodiment of the present invention.

Referring to FIG. 11, different views are illustrated of a cannulated drill 1100 according to an exemplary embodiment of the present invention. The cannulated drill 1100 can be utilized with the drill guide and washer holder 1000 to drill a pilot hole in a bone to receive the cannulated bone screw 800. The cannulated drill 1100 includes a drill bit 1102 which in an exemplary embodiment may be 4 mm. The drill bit 1102 can be removable from the cannulated drill 1100 through a coupling mechanism 1104 disposed to an end of the cannulated drill 1100. The coupling mechanism 1104 is disposed to a cylinder member 1106 which extends to a drill connection point 1108. The drill connection point 1108 includes a connector 1110 for interfacing to a drill element. The connector 1110 translates a rotational force from the drill element through the cylinder member 1106 to enable the drill bit 1102 to rotate for drilling the pilot hole in a bone. For example, the cannulated drill 1100 can be utilized in the drill opening 1010 of the drill guide and washer holder 1000.

Figure 12:
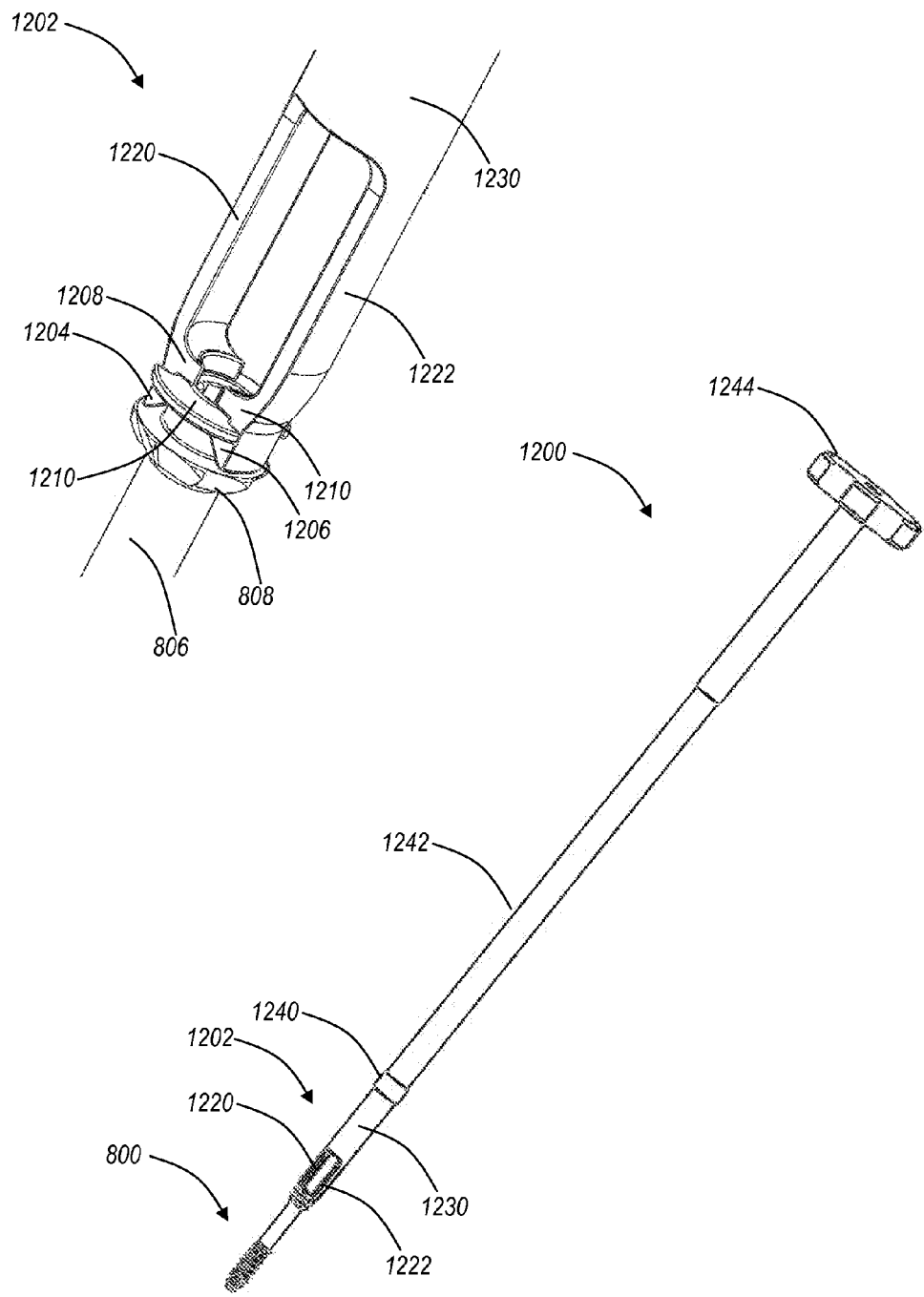
FIG. 12 illustrates different views of a screw holder assembly 1200 and a screw holder for the cannulated bone screw of FIG. 8 according to an exemplary embodiment of the present invention.

Referring to FIG. 12, different views are illustrated of a screw holder assembly 1200 and a screw holder 1202 for the cannulated bone screw 800 according to an exemplary embodiment of the present invention. The screw holder 1202 is operable to engage the screw head 810 through the keyed head flanges 812 on the cannulated bone screw 800. For example, the screw holder 1202 can utilize similar mechanisms as described herein in FIG. 5. The screw holder 1202 is configured to snap over the keyed head flanges 812 in the screw head 810. The screw holder 1202 includes a first arc member 1204 and a second arc member 1206, each configured to engage one of the keyed head flanges 812 in the screw head 810. The arc members 1204, 1206 each include a notch (not shown) which snaps on the keyed head flanges 812, and a top of the arc members 1204, 1206 substantially mates with a top side of the toothed surface 808. The screw holder 1202 further includes a first arc portion 1208 and a second arc portion 1210 offset from the arc members 1204, 1206. The arc portions 1208, 1210 are operable to engage a top 1212 of the screw head 810 when the arc members 1204, 1206 are engaged to the keyed head flanges 812. Collectively, the arc members 1204, 1206 and the arc portions 1208, 1210 define notches which are operable to engage the keyed head flanges 812. In the engaged position, the screw holder 1202 is operable to translate a rotational force to the cannulated bone screw 800 to enable engagement of the washer 802 and a bone, such as through a pilot hole. The screw holder 1202 also further includes a first support member 1220 and a second support member 1222. Each of the support members 1220, 1222 are disposed to the arc members 1204, 1206, and the arc portions 1208, 1210 extend from the support members 1220, 1222. The support members 1220, 1222 are disposed to a cylinder member 1230.

The screw holder assembly 1200 is operable to engage the screw holder 1202 through a coupling mechanism 1240. The coupling mechanism 1240 can be disposed to the screw holder 1202, to a cylinder member 1242, or to neither. The cylinder member 1242 extends to a handle 1244. A surgeon can utilize the handle 1244 while griping onto the cylinder member 1242 to maneuver the screw holder assembly 1200 to engage the cannulated bone screw 800, to position the cannulated bone screw 800 into a washer 802 and pilot hole, and to screw the cannulated bone screw 800 into the bone.

Figure 13:
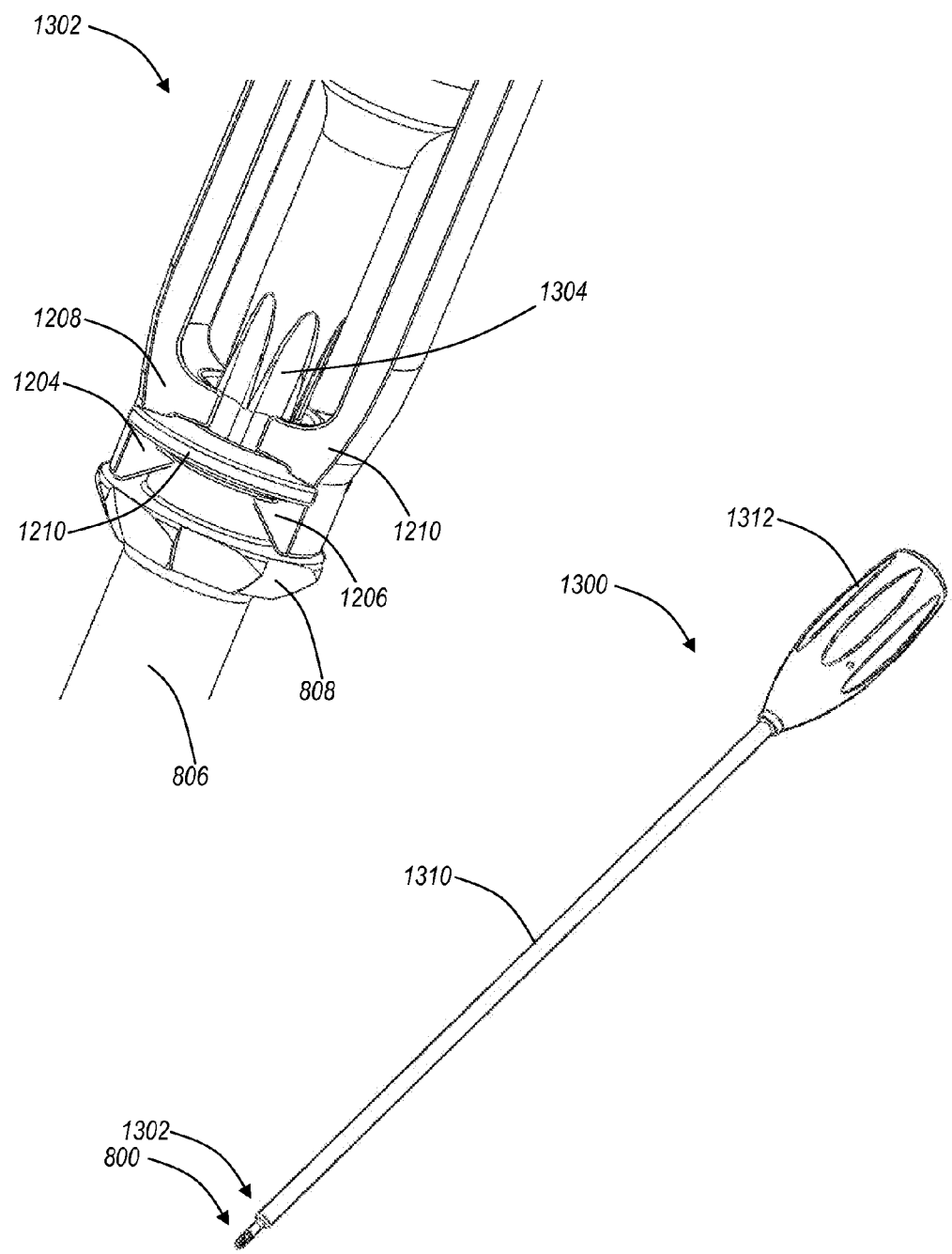
FIG. 13 illustrates a screw driver with a hexalobular design according to an exemplary embodiment of the present invention.

Referring to FIG. 13, a screw driver assembly 1300 is illustrated with a hexalobular design 1304 for a screw holder 1302 according to an exemplary embodiment of the present invention. The screw holder 1302 is operable to engage the screw head 810 through the keyed head flanges 812 and through a hexalobular design 1304 on the cannulated bone screw 800. The screw driver assembly 1300 is similar to the screw holder assembly 1200 with the addition of the hexalobular design 1304. The screw driver assembly 1300 includes a cylinder member 1310 and a handle 1312. The cylinder member 1310 includes the screw holder 1302 at one end and the handle 1312 at the other end.

Figure 14:
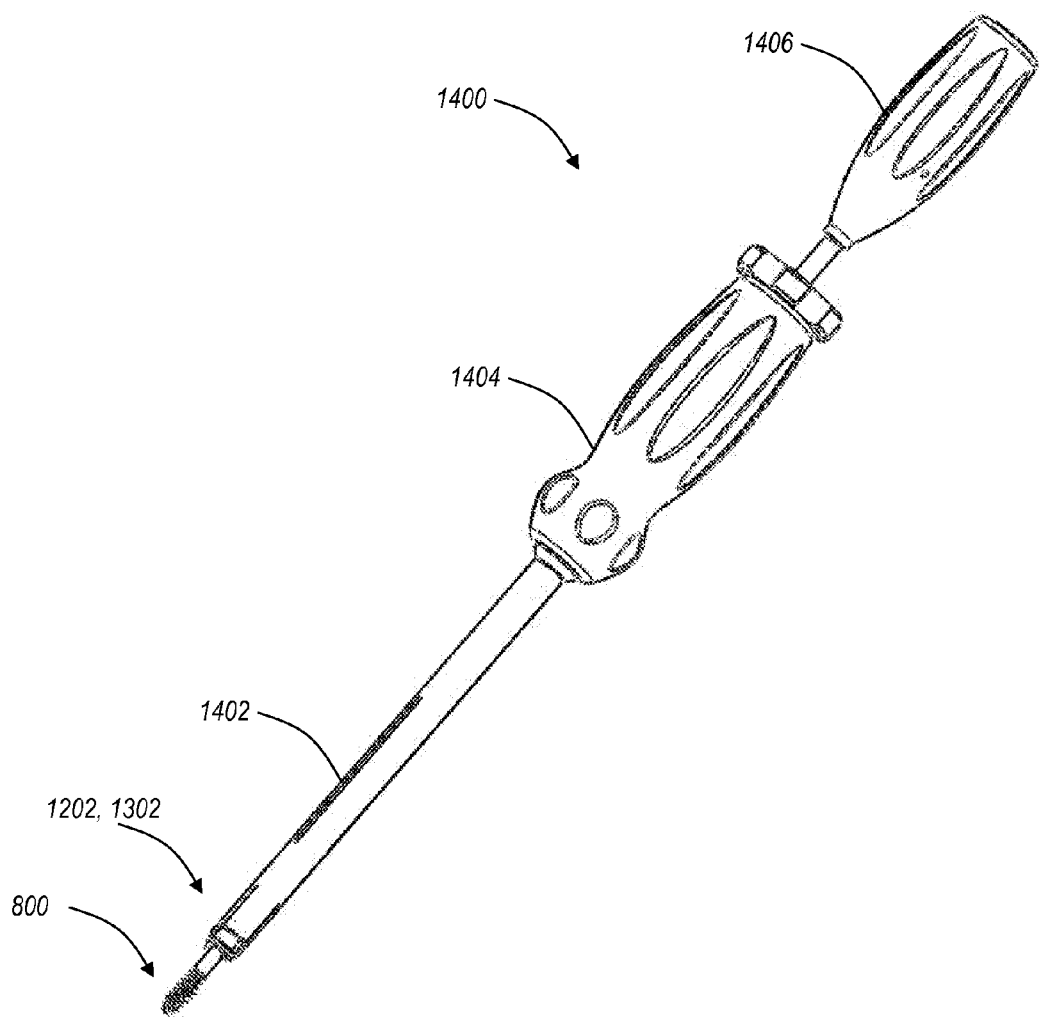
FIG. 14 illustrates a rescue screw system according to an exemplary embodiment of the present invention.

Referring to FIG. 14, a rescue screw system 1400 is illustrated according to an exemplary embodiment of the present invention. The rescue screw system 1400 is operable to remove an inserted cannulated bone screw 800. The rescue screw system 1400 includes one of the screw holders 1202, 1302, a cylinder member 1402 disposed to the screw holder 1202, 1302 at one end and to a grip portion 1404 at another end, and a handle portion 1406 disposed to the grip portion 1404. A surgeon can utilize the rescue screw system 1400 to engage the cannulated bone screw 800 and remove the cannulated bone screw 800 through rotational force applied through the grip portion 1404 and the handle portion 1406.

Figure 15:
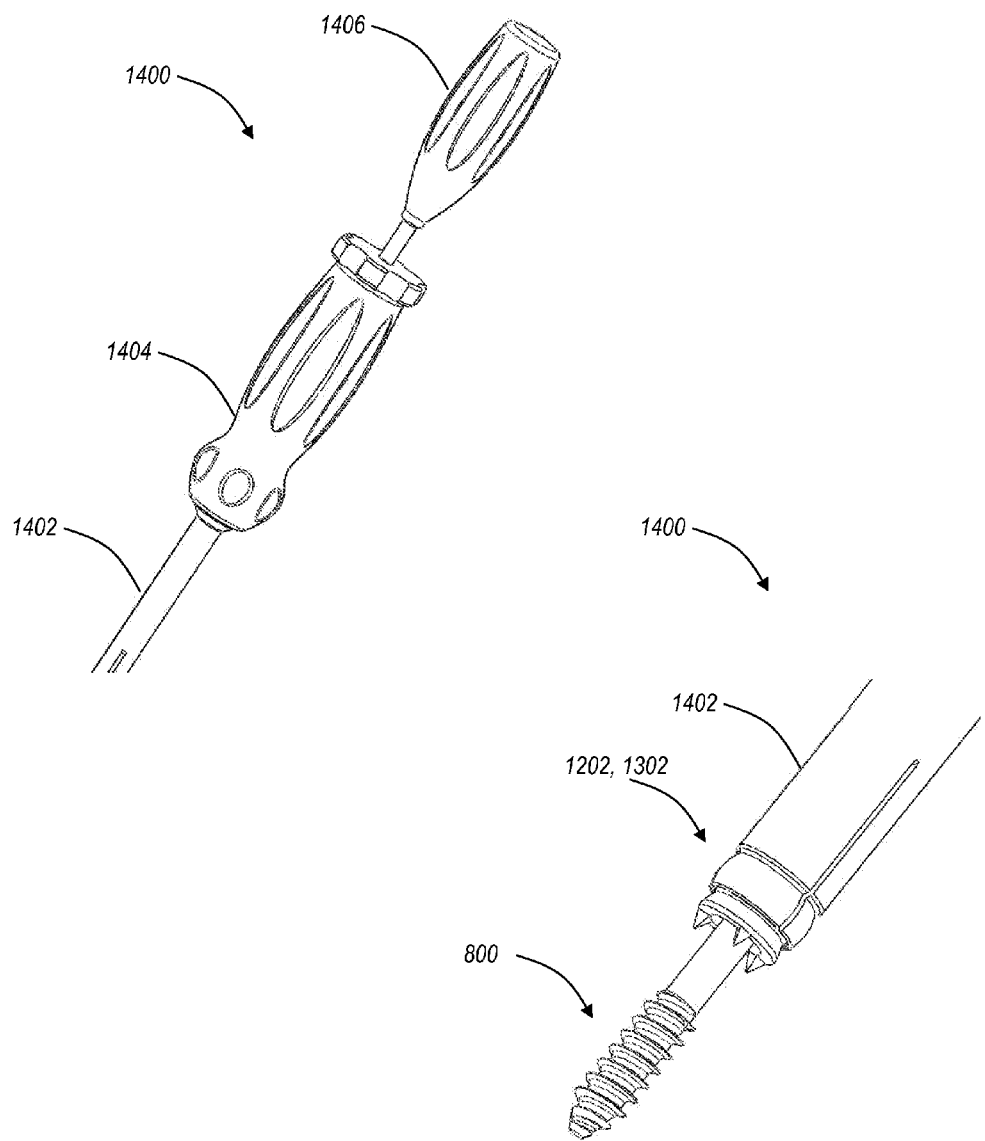
FIG. 15 illustrates different views of the rescue screw system of FIG. 14 according to an exemplary embodiment of the present invention.

Referring to FIG. 15, different views are illustrated of the rescue screw system 1400 of FIG. 14 according to an exemplary embodiment of the present invention. FIG. 15 illustrates a close-up view of the handle portion 1406 and the grip portion 1404, and a close-up view of the cannulated bone screw 80 engaged to the screw holder 1202, 1302.

Although the present invention has been illustrated and described herein with reference to preferred embodiments and specific examples thereof, it will be readily apparent to those of ordinary skill in the art that other embodiments and examples may perform similar functions and/or achieve like results. All such equivalent embodiments and examples are within the spirit and scope of the present invention, are contemplated thereby, and are intended to be covered by the following claims.

The invention claimed is:

1. A biomedical implant fastener system, comprising:
a fastener comprising a first plurality of teeth; and
a washer comprising a second plurality of teeth configured to be engaged with the first plurality of teeth, wherein the first plurality of teeth and the second plurality of teeth are configured such that, when the first plurality of teeth is engaged with the second plurality of teeth, the fastener is allowed to pivot with respect to the washer while still preventing the fastener from backing out of the washer.

2. The biomedical implant fastener system of claim 1, wherein the fastener comprises a bone screw.

3. The biomedical implant fastener system of claim 2, wherein the bone screw comprises a cannulated bone screw.

4. The biomedical implant fastener system of claim 2, wherein the washer further comprises a frictional surface positioned along a lower surface of the washer that is configured for engaging a bony structure below the washer.

5. The biomedical implant fastener system of claim 4, wherein the frictional surface comprises a plurality of spikes.

6. The biomedical implant fastener system of claim 1, wherein the biomedical implant fastener system is configured to be used with at least one of a thoracolumbar fixation plate, an anterior lumbar fixation plate, a stand-alone intervertebral spacer, a bone fracture fixation plate, and a spinal fixation system comprising a pedicle screw.

7. The biomedical implant fastener system of claim 1, wherein the fastener further comprises a fastener head, and wherein the fastener head is spaced apart from the first plurality of teeth.

8. The biomedical implant fastener system of claim 1,
wherein the first plurality of teeth is rigidly affixed to an inferior convex surface of the fastener; and
wherein the second plurality of teeth is positioned on a superior concave surface of the washer.

9. The biomedical implant fastener system of claim 1, wherein the first plurality of teeth comprises a radial toothed pattern.

10. The biomedical implant fastener system of claim 1, wherein the fastener comprises a bone screw, and wherein the bone screw is configured to be driven into the washer positioned at a pilot hole in a bone at an angle with respect to an opening in the washer.

11. A biomedical implant fastener system, comprising:
a fastener comprising a first plurality of teeth; and
a washer comprising a second plurality of teeth configured to be engaged with the first plurality of teeth, wherein the first plurality of teeth is configured to engage with the second plurality of teeth such that so as to allow for selective rotation between the washer and the fastener in a first rotational direction and so as to prevent rotation between the washer and the fastener in a second rotational direction opposite from the first rotational direction when the fastener is engaged with the washer such that the second plurality of teeth is engaged with the first plurality of teeth.

12. The biomedical implant fastener system of claim 11, wherein the first plurality of teeth and the second plurality of teeth are configured to engage with one another such that, when the first plurality of teeth is engaged with the second plurality of teeth, the washer is allowed to at least one of conform and pivot with respect to the fastener.

13. The biomedical implant fastener system of claim 11, wherein the fastener comprises a bone screw, and wherein the bone screw is configured to at least one of conform and pivot with respect to the washer when the first plurality of teeth is engaged with the second plurality of teeth in order to accommodate different bone morphologies.

14. The biomedical implant fastener system of claim 11, wherein the system is configured such that the fastener can be placed at variable conical angles with respect to the washer when the first plurality of teeth is engaged with the second plurality of teeth.

15. A bone screw system, comprising:
a bone screw comprising a first plurality of teeth and a threaded portion configured to engage a bony structure, wherein the first plurality of teeth is rigidly affixed to the bone screw, and wherein the threaded portion is spaced apart from the first plurality of teeth; and
a washer comprising an interior portion comprising a second plurality of teeth, wherein the first plurality of teeth and the second plurality of teeth are configured to mate to prevent the bone screw from backing out of the washer, and such that, when the first plurality of teeth is engaged with the second plurality of teeth, allowing at least one of the bone screw and the washer to at least one of conform and pivot in order to accommodate different bone morphologies.

16. The bone screw system of claim 15, wherein the bone screw further comprises a bone screw head, wherein the bone screw head is spaced apart from the first plurality of teeth, and wherein the first plurality of teeth is oriented away from the bone screw head.

17. The bone screw system of claim 15, wherein the washer comprises a frictional surface configured for engaging the bony structure.

18. The bone screw system of claim 15, wherein the first plurality of teeth comprise uni-directional teeth, and wherein the second plurality of teeth comprise uni-directional teeth.

19. The bone screw system of claim 15, wherein the first plurality of teeth and the second plurality of teeth are configured to mate to allow the bone screw to advance and rotate in a first direction, and wherein the first plurality of teeth and the second plurality of teeth are further configured prevent the bone screw from rotating in a second direction opposite from the first direction once the first plurality of teeth has been engaged with the second plurality of teeth.

20. The bone screw system of claim 15, wherein the bone screw further comprises a non-threaded section.

21. The bone screw system of claim 20, wherein the non-threaded section is positioned between the threaded section and the first plurality of teeth.

22. The bone screw system of claim 21, wherein the bone screw is configured such that the non-threaded section is configured to engage a first bony portion and such that the threaded section is configured to engage a second bony portion.

* * * * *